(12) United States Patent
Jang et al.

(10) Patent No.: US 11,883,508 B2
(45) Date of Patent: Jan. 30, 2024

(54) METHOD FOR CULTURING 3-DIMENSIONAL LUNG CANCER ORGANOID AND METHOD FOR PREPARING PATIENT-DERIVED XENOGRAFT ANIMAL MODEL USING SAME

(71) Applicant: ONCOCLEW CO., LTD., Seoul (KR)

(72) Inventors: Se Jin Jang, Seongnam-si (KR); Min Suh Kim, Seoul (KR); Young Ah Suh, Seoul (KR); Hye Min Mun, Seoul (KR); Ju Hee Oh, Anseong-si (KR)

(73) Assignee: ONCOCLEW CO., LTD., Seoul (KR)

( * ) Notice: Subject to any disclaimer, the term of this patent is extended or adjusted under 35 U.S.C. 154(b) by 540 days.

(21) Appl. No.: 16/638,801

(22) PCT Filed: Aug. 13, 2018

(86) PCT No.: PCT/KR2018/009254
§ 371 (c)(1),
(2) Date: Feb. 13, 2020

(87) PCT Pub. No.: WO2019/035618
PCT Pub. Date: Feb. 21, 2019

(65) Prior Publication Data
US 2021/0128752 A1 May 6, 2021

(30) Foreign Application Priority Data

Aug. 14, 2017 (KR) ........................ 10-2017-0103121

(51) Int. Cl.
*A61K 49/00* (2006.01)
*A01K 67/027* (2006.01)
*C12N 5/09* (2010.01)

(52) U.S. Cl.
CPC ...... *A61K 49/0008* (2013.01); *A01K 67/0271* (2013.01); *C12N 5/0693* (2013.01); *A01K 2207/12* (2013.01); *A01K 2227/105* (2013.01); *A01K 2267/0331* (2013.01); *C12N 2500/38* (2013.01); *C12N 2501/11* (2013.01); *C12N 2501/113* (2013.01); *C12N 2501/115* (2013.01); *C12N 2501/727* (2013.01); *C12N 2513/00* (2013.01); *C12N 2533/50* (2013.01)

(58) Field of Classification Search
None
See application file for complete search history.

(56) References Cited

U.S. PATENT DOCUMENTS

2017/0285002 A1* 10/2017 Taniguchi .............. A61K 35/44
2021/0147810 A1    5/2021 Sabaawy et al.

FOREIGN PATENT DOCUMENTS

| KR | 20140133399 | 11/2014 |
|---|---|---|
| WO | WO 2016015158 | 2/2016 |
| WO | WO 2016/093359 | 6/2016 |
| WO | WO 2016083613 | 6/2016 |
| WO | WO 2016112172 | 7/2016 |

OTHER PUBLICATIONS

Del Bufalo et al. "3D modeling of human cancer: A PEG-fibrin hydrogel system to study the role of tumor microenvironment and recapitulate the in vivo effect of oncolytic adenovirus." Biomaterials 84 (2016): 76-85. (Year: 2016).*
Liu et al. "Tumor engineering: orthotopic cancer models in mice using cell-loaded, injectable, cross-linked hyaluronan-derived hydrogels." Tissue Engineering 13.5 (2007): 1091-1101. (Year: 2007).*
Barkauskas et al., "Lung organoids: current uses and future promise" *The Company of Biologists:Development* 2017, 144, 986-997.
DeRosa et al., "Patient-Derived Models of Human Breast Cancer: Protocols for In Vitro and In Vivo Applications in Tumor Biology and Translational Medicine" *Current Protocols in Pharmacology* 2013, 14.23.1-14.23.43.
Dutta et al., "Disease Modeling in Stem Cell-Derived 3D Organoid Systems" *Trends in Molecular Medicine* 2017, 23(5), 393-41o.
Huo et al., "Patient-derived cell Hoe, xenograft and organoid models in long cancer therapy" *Transl Lung Cancer Res* 2020, 9(5), 2214-2232.
Ilie et al., "Setting up a wide panel of patient-derived tumor xenografts of non-small cell lung cancer by improving the preanalytical steps" *Cancer Medicine* 2015, 4{2), 201-211.
Kim et al., "Patient-derived lung cancer organoids as in vitro cancer models for therapeutic screening" *Nature Communications* 2019, 10:399, 15 pages.

* cited by examiner

*Primary Examiner* — Emily A Cordas
(74) *Attorney, Agent, or Firm* — NORTON ROSE FULBRIGHT US LLP

(57) ABSTRACT

The present invention relates to a method for culturing a 3-dimensional lung cancer organoid and a method for preparing a patient-derived xenograft animal model using the same. More specifically, the present invention relates to a method for culturing a 3-dimensional lung cancer organoid, a lung cancer organoid prepared by the method, a medium composition for culturing the lung cancer organoid, a method for preparing a xenograft animal model using the lung cancer organoid, a patient-derived lung cancer organoid xenograft animal model prepared by the method, and a method for analyzing therapeutic efficacy of an anticancer agent and a method for screening an anticancer agent, using the animal model.

6 Claims, 5 Drawing Sheets

Scale bar: 200um

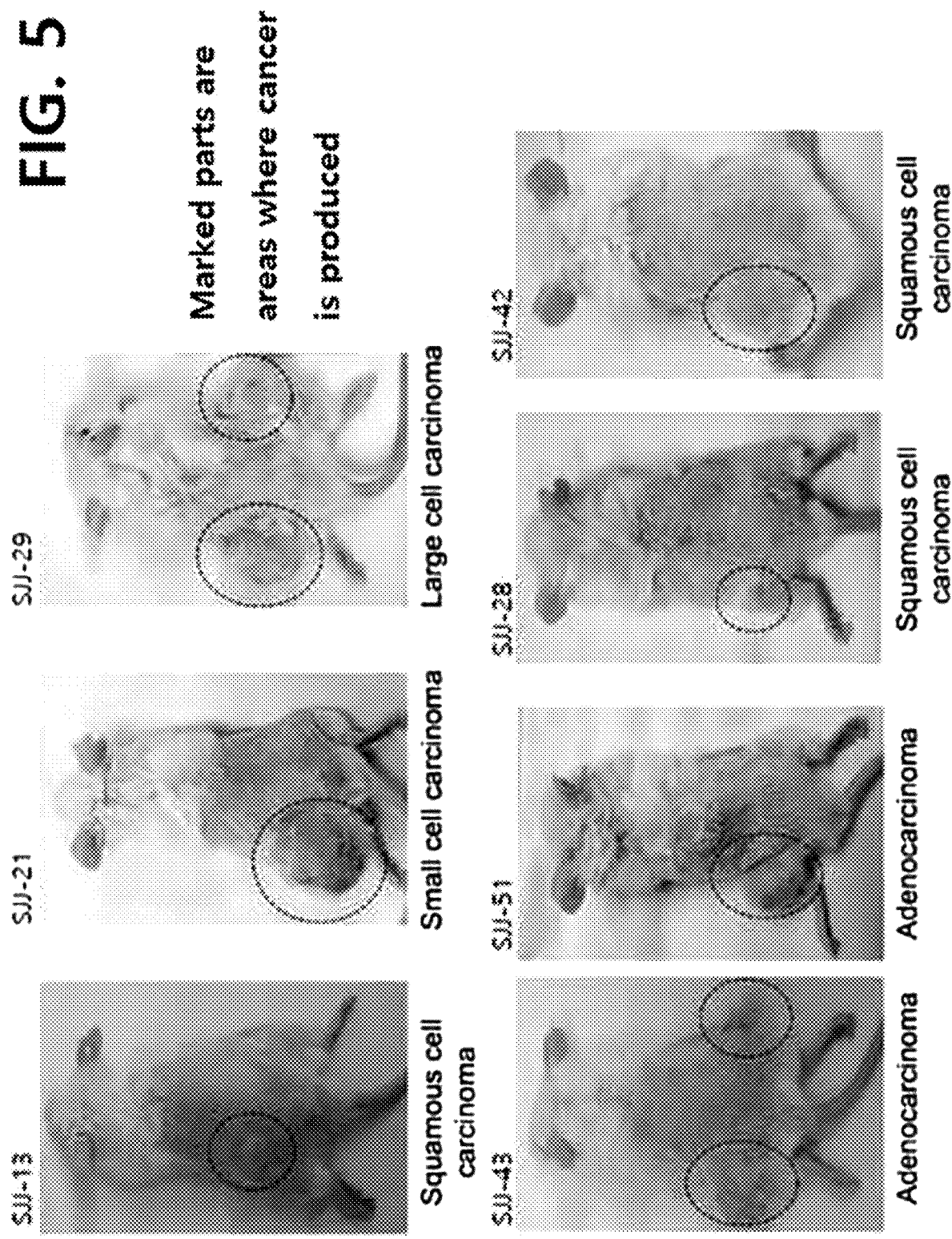

METHOD FOR CULTURING 3-DIMENSIONAL LUNG CANCER ORGANOID AND METHOD FOR PREPARING PATIENT-DERIVED XENOGRAFT ANIMAL MODEL USING SAME

TECHNICAL FIELD

The present invention relates to a method for culturing a 3-dimensional lung cancer organoid and a method for preparing a patient-derived xenograft animal model using the same. More specifically, the present invention relates to a method for culturing a 3-dimensional lung cancer organoid, a lung cancer organoid prepared by the method, a medium composition for culturing the lung cancer organoid, a method for preparing a xenograft animal model using the lung cancer organoid, a patient-derived lung cancer organoid xenograft animal model prepared by the method, and a method for analyzing therapeutic efficacy of an anticancer agent and a method for screening an anticancer agent, using the animal model.

BACKGROUND ART

In cancer research, cancer models that well represent the patient's characteristics are important. Cancer models that have been used mainly in vitro until now are cancer cell lines. Cancer cell lines are models prepared by adapting patient's cancer tissue-derived cancer cells to 2-dimensional culture, which have advantages of being not only easily handled experimentally, but also suitable for performing many genetic and pharmacological screenings at once. However, for cancer cell lines, a success rate at which cancer cells are constructed from cancer tissue is low, and long-term 2-dimensional passage of patient-derived cancer cells results in disappearance of properties, which may occur in histological structures, such as heterogeneity or mutations observed in the patient's cancer. Thus, cancer cell lines have a problem that even if cell lines having lost heterogeneity are used and injected into immunodeficient mice to prepare cancer models, such models cannot represent the patient's original characteristics.

As a model to compensate for this drawback of cancer cell lines, an in vivo-based patient-derived xenograft (PDX) model has been developed. The PDX model uses a method in which a part of the patient's cancer tissue is directly transplanted into immunodeficient mice. This model is evaluated as a model which not only well represents structure, metastasis, and various gene expressions, observed in the patient's cancer tissue, but also enables preliminary prediction of drug reactivity in clinical trials. However, there is a disadvantage that it takes as little as two months to as long as six months to obtain a successful PDX model. In particular, in a case of lung cancer, a success rate of PDX model is very low (less than 20%) as compared with colorectal cancer, and a period of 10 months or longer is also needed. Thus, a PDX model was determined to be unsuitable for the purpose of testing patient-specific anticancer agents. In addition, the PDX model has a disadvantage that inter-species contamination occurs, and has a problem of gradually losing the original human tissue environment while performing culture through several passages for maintaining and using a cancer model of a specific patient.

In Korean Patent No. 10-1674468, cancer tissues are isolated from cancer patients, and subjected to primary culture and proliferation. Then, a certain amount of cancer cell line is injected into immunodeficient mice to prepare an animal model having the same morphology and genetic information as the original patient.

However, there have been no reports of xenograft animal models prepared by isolating cancer tissue from a lung cancer patient, performing culture so that a 3-dimensional organoid is formed, and then transplanting the organoid into immunodeficient mice while maintaining the organoid's structural form.

SUMMARY OF THE INVENTION

The present invention is intended to solve the above problems, and an object of the present invention is to provide a method for culturing a 3-dimensional lung cancer organoid, comprising the steps of: (a) cellizing lung cancer tissue isolated from a lung cancer patient and then culturing the cellized lung cancer cells with a cell culture substrate, to obtain a lung cancer organoid; (b) subjecting the obtained organoid to treatment with an enzyme and then allowing reaction to proceed; and (c) adding, to the lung cancer organoid after step (b), a cell culture substrate and performing culture so that a 3-dimensional lung cancer organoid is formed.

Another object of the present invention is to provide a lung cancer organoid prepared by the culture method.

Yet another object of the present invention is to provide a medium composition for culturing a lung cancer organoid, including a culture medium composition that contains B27 supplement, N2 supplement, human epidermal growth factor, and human fibroblast growth factor.

Still yet another object of the present invention is to provide a method for preparing a patient-derived lung cancer organoid xenograft animal model, comprising the steps of: (a) cellizing lung cancer tissue isolated from a lung cancer patient and then culturing the cellized lung cancer cells with a cell culture substrate, to obtain a lung cancer organoid; (b) subjecting the obtained organoid to treatment with an enzyme and then allowing reaction to proceed; (c) culturing the enzyme-treated organoid on a plate, to which a cell culture substrate has been added, so that a 3-dimensional lung cancer organoid is formed; (d) removing the cell culture substrate from the lung cancer organoid; (e) encapsulating the organoid, from which the cell culture substrate has been removed, in a membrane and then solidifying the same; and (f) transplanting, into a subject animal, the lung cancer organoid obtained in step (e).

Still yet another object of the present invention is to provide a patient-derived lung cancer organoid xenograft animal model prepared by the above method.

Still yet another object of the present invention is to provide a method for analyzing therapeutic efficacy of an anticancer agent using a patient-derived lung cancer organoid xenograft animal model, comprising the steps of: (a) administering an anticancer agent to the patient-derived lung cancer organoid xenograft animal model; and (b) analyzing growth or metastasis of lung cancer cells in the animal model to determine therapeutic efficacy of the anticancer agent.

Still yet another object of the present invention is to provide a method for screening an anticancer agent using a patient-derived lung cancer organoid xenograft animal model, comprising the steps of: (a) administering an anticancer agent candidate to the patient-derived lung cancer organoid xenograft animal model; and (b) analyzing growth or metastasis of lung cancer cells in the animal model to determine therapeutic efficacy of the anticancer agent candidate.

The present inventors have found that histological characteristics of cancer are maintained in a patient-derived xenograft animal model, which has been obtained by cellizing a part of lung cancer tissue isolated from a patient, culturing the resulting lung cancer cells so that an organoid in the form of having a 3-dimensional tissue structure is formed, and transplanting the organoid directly into mice while maintaining the organoid's 3-dimensional structure, thereby completing the present invention.

In the present specification, "lung cancer tissue" and "lung cancer cell" are used in the same concept as "tumor tissue" and "tumor cell".

BRIEF DESCRIPTION OF DRAWINGS

FIG. 5 illustrates photographs that identify tumor formation in xenograft animal models prepared according to an embodiment of the present invention and comparative examples.

DETAILED DESCRIPTION OF THE INVENTION

Figure 1:
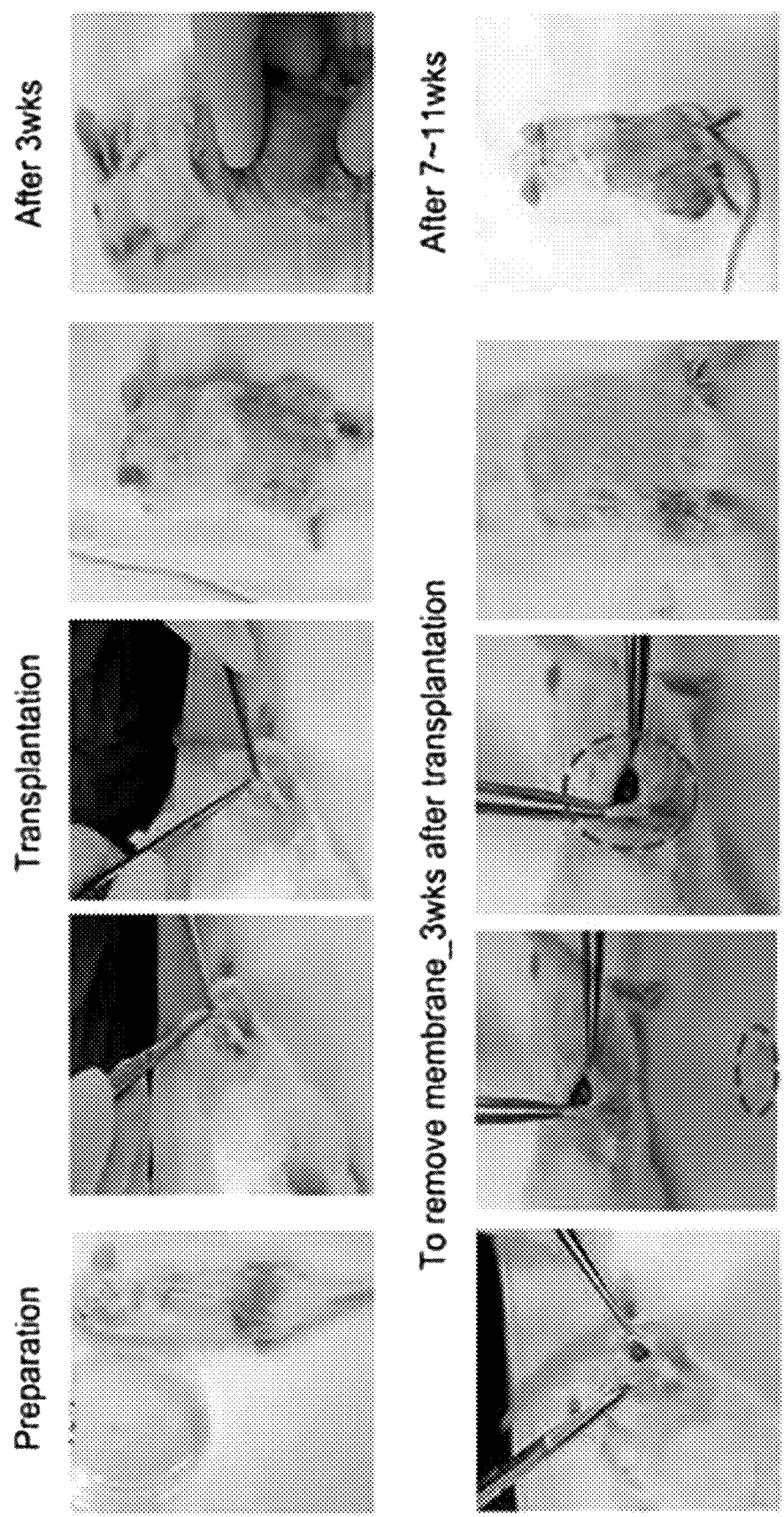
FIG. 1 illustrates photographs showing a process in which a patient-derived lung cancer organoid according to an embodiment of the present invention is transplanted into an immunodeficient mouse.

Hereinafter, the present invention will be described in detail.

In an aspect of the present invention, there is provided a method for culturing a 3-dimensional lung cancer organoid, comprising the steps of: (a) cellizing lung cancer tissue isolated from a lung cancer patient and then culturing the cellized lung cancer cells with a cell culture substrate, to obtain a lung cancer organoid; (b) subjecting the obtained organoid to treatment with an enzyme and then allowing reaction to proceed; and (c) adding, to the lung cancer organoid after step (b), a cell culture substrate and performing culture so that a 3-dimensional lung cancer organoid is formed.

First, the method for culturing a 3-dimensional lung cancer organoid according to the present invention comprises a step [step (a)] of cellizing lung cancer tissue isolated from a lung cancer patient and then culturing the cellized lung cancer cells with a cell culture substrate, to obtain a lung cancer organoid.

The lung cancer cells of the present invention may be obtained through cellization of lung cancer tissue isolated from a lung cancer patient according to a known protocol.

The cell culture substrate of the present invention may include MATRIGEL®, collagen, alginate, agarose, gelatin, fibrin, hyaluronic acid, chitosan, or a mixture of two or more thereof, and the cell culture substrate may preferably be MATRIGEL®. However, the cell culture substrate is not limited thereto, and any cell culture substrate may be used as long as it is a cell culture substrate used in the art for organoid culture.

As used herein, the term "MATRIGEL®" refers to a protein complex (product name of BD BIOSCIENCES®) extracted from sarcoma cells of an EHS (Engelbreth-Holm-Swarm) mouse, and contains extracellular matrix (ECM) such as laminin, collagen, and heparin sulfate proteoglycan, and growth factors such as fibroblast growth factor (FGF), epidermal growth factor (EGF), insulin-like growth factor (IGF), transforming growth factor-beta (TGF-β), and platelet-derived growth factor (PDGF). The complex that makes up MATRIGEL® provides a complex extracellular environment found in many tissues, which allows MATRIGEL® to be used as a substrate for cell culture.

The organoid culture step of the present invention may be carried out using a medium composition that contains B27 supplement, N2 supplement, human epidermal growth factor (hEGF), and human fibroblast growth factor (hFGF).

The medium composition may further contain Rho-associated protein kinase (ROCK) inhibitor. The ROCK inhibitor may include, but is not limited to, Y-27632 ((1R,4r)-4-((R)-1-aminoethyl)-N-(pyridin-4-yl) cyclohexanecarboxamide). The ROCK inhibitor plays a role in inhibiting apoptosis and cell differentiation, and the size and shape of an organoid may vary depending on presence or absence of the ROCK inhibitor.

Next, the culture method according to the present invention comprises a step [step (b)] of subjecting the obtained organoid to treatment with an enzyme and then allowing reaction to proceed.

Specifically, the enzyme is to separate the organoid into organoids having a microstructure or single cells, for passages to generate an organoid having a 3-dimensional structure. For the enzyme, a reagent containing trypsin may be used. Preferably, Trypsin/EDTA or TRYPLE™ Express may be used. However, the enzyme is not limited thereto.

Here, in a case of using Trypsin/EDTA as the enzyme, the reaction time is preferably 10 to 15 minutes; and in a case of using TRYPLE™ Express as the enzyme, the reaction time is preferably 15 to 20 minutes. In a case where the reaction time is shorter than the above range, there is a problem that the organoid having a 3-dimensional structure is not separated into organoids having a microstructure or single cells; and in a case where the reaction time is longer than the above range, there is a problem that the entire organoid having a 3-dimensional structure is separated into single cells or unexpected cell damage may occur.

In an embodiment of the present invention, the method may further comprise a step of removing the cell culture substrate from the organoid culture plate before the enzyme treatment step. Here, for the removal step, a method of performing centrifugation so that the organoid is detached from the cell culture substrate may be used. The organoid detached from the cell culture substrate precipitates due to gravity, which allows for easy layer separation.

Finally, the culture method according to the present invention comprises a step [step (c)] of adding, to the lung cancer organoid, a cell culture substrate and performing culture so that a 3-dimensional lung cancer organoid is formed.

Specifically, in the culture step, the organoid may be dispensed into each well of the well plate to which the cell culture substrate has been added, and then cultured until the cells are caused to form a 3-dimensional shape. The organoid may be dispensed, per well, at an amount of 10 to 100 μl and preferably 20 to 70 μl; however, the present invention is not limited thereto. Here, in a case where the amount of the organoid dispensed is less than the above range, there is a problem that the cells do not grow properly due to insufficient cell number per drop-in. In a case where the amount of the organoid dispensed exceeds the above range, there is a problem that the number of cells per drop-in is excessive, so that the cells are detached from the cell culture substrate or have difficulty in forming a 3-dimensional structure.

In addition, the organoid of the present invention may be cultured for 7 to 21 days until the 3-dimensional structure is formed, and the culture is preferably performed for 14 to 18 days. However, the present invention is not limited thereto. Here, in a case where the culture period is shorter than the above range, there is a problem that the cells do not grow into an organoid having a size enough to be transplantable. In a case where the culture period is longer than the above range, there is a problem that cell aging occurs due to long-term culture.

In addition, in the present invention, the 3-dimensional shape of the organoid is preferably formed in a spherical shape. However, the present invention is not limited thereto.

In an embodiment of the present invention, the organoid culture step may be carried out in a medium composition for culturing a lung cancer organoid, the medium composition containing B27 supplement, N2 supplement, human epidermal growth factor, and human fibroblast growth factor. The medium composition may further contain ROCK inhibitor. However, the present invention is not limited thereto.

In another aspect of the present invention, there is provided a lung cancer organoid prepared by the above method.

As used herein, the term "organoid" refers to a miniature organ made by culturing or recombining stem cells or cells isolated from organ cells. In the present invention, a patient-derived lung cancer organoid has been prepared by cellizing tissue isolated from a lung cancer patient and performing culture using a medium composition according to the present invention.

Therefore, the lung cancer organoid according to the present invention is obtained by performing 3-dimensional culture of a part of cancer tissue collected from a lung cancer patient, and mass production thereof may be achieved by storing the constructed line of patient-derived lung cancer organoid or continuously performing culture.

In yet another aspect of the present invention, there is provided a medium composition for culturing a lung cancer organoid, the medium composition including a culture medium composition that contains B27 supplement, N2 supplement, human epidermal growth factor, and human fibroblast growth factor.

Specifically, the culture medium may be, but is not limited to, DMEM/F12, Minimum Essential Media Eagle (MEME), Alpha MEM (MEM, Alpha Modification), Basal Media Eagle (BME), Dulbecco's Modified Eagle's Media (DMEM), F-12 Nutrient Mixture (Ham's F12), Iscove's Modified Dulbecco's Media (IMDM), Media 199 (M199), McCoy's 5A Media, or MCDB Media, with DMEM/F12 medium being preferred.

The culture medium of the present invention may further contain ROCK inhibitor. The ROCK inhibitor may include, but is not limited to, Y-27632 ((1R,4r)-4-((R)-1-aminoethyl)-N-(pyridin-4-yl)cyclohexanecarboxamide).

The culture medium of the present invention may further contain antibiotics. Here, examples of the antibiotics may include, but are not limited to, penicillin, streptomycin, penicillin/streptomycin (P/S), ampicillin, or cephalosporin. Addition of antibiotics to the culture medium of the present invention may prevent contamination caused by exogenous bacteria, fungi, mycoplasma, and yeast, and the like.

In still yet another aspect of the present invention, there is provided a method for preparing a patient-derived lung cancer organoid xenograft animal model, comprising the steps of: (a) cellizing lung cancer tissue isolated from a lung cancer patient, and then culturing the cellized lung cancer cells with a cell culture substrate, to obtain a lung cancer organoid; (b) subjecting the obtained organoid to treatment with an enzyme and then allowing reaction to proceed; (c) adding, to the lung cancer organoid after step (b), a cell culture substrate, and performing culture so that a 3-dimensional lung cancer organoid is formed; (d) removing the cell culture substrate from the lung cancer organoid; (e) encapsulating the organoid, from which the cell culture substrate has been removed, in a membrane and then solidifying the same; and (f) transplanting, into a subject animal, the lung cancer organoid obtained in step (e).

FIG. 1 illustrates a method for preparing a patient-derived lung cancer organoid xenograft animal model according to the present invention.

First, the method for preparing a patient-derived lung cancer organoid xenograft animal model according to the present invention comprises steps [steps (a) to (c)] of: cellizing lung cancer tissue isolated from a lung cancer patient and then culturing the cellized lung cells with a cell culture substrate, to obtain a lung cancer organoid, according to the method for culturing a 3-dimensional lung cancer organoid of the present invention; subjecting the obtained organoid to treatment with an enzyme and then allowing reaction to proceed; and adding, to the lung cancer organoid, a cell culture substrate, and performing culture so that a 3-dimensional lung cancer organoid is formed.

Details of the method for preparing a 3-dimensional lung cancer organoid are as described above.

Next, the method for preparing a xenograft animal model according to the present invention comprises a step [step (d)] of removing the cell culture substrate from the lung cancer organoid. The cell culture substrate may be MATRIGEL®, and details thereof are as described above.

Next, the method for preparing a xenograft animal model according to the present invention comprises a step [step (e)] of encapsulating the organoid, from which the cell culture substrate has been removed, in a membrane and then solidifying the same.

Specifically, the membrane of the present invention may be biocompatible or biodegradable. The term "biocompatible material" as used herein refers to a material that is substantially non-toxic to the human body, chemically inert, and not immunogenic, and the term "biodegradable material" as used herein refers to a material that may be degraded by body fluids or microorganisms in the living body. In the preparation method of the present invention, the membrane serves to maintain the 3-dimensional shape of a lung cancer organoid after the lung cancer organoid is transplanted into an animal.

Here, as the biocompatible or biodegradable material, hyaluronic acid, polyester, polyhydroxyalkanoates (PHAs), poly($\alpha$-hydroxyacid), poly($\beta$-hydroxyacid), poly(3-hydroxybutyrate-co-valerate; PHBV), poly(3-hydroxypropionate; PUP), poly(3-hydroxyhexanoate; PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazenes, PHA-PEG, ethylene vinyl alcohol copolymer (EVOH), polyurethane, silicone, polyester, polyolefin, polyisobutylene and ethylene-alphaolefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, alginate, inulin, starch, or glycogen may be used; and hyaluronic acid, polyester, polyhydroxyalkanoates (PHAs), poly($\alpha$-hydroxyacid), poly($\beta$-hydroxyacid), poly(3-hydroxybutyrate-co-valerate; PHBV), poly(3-hydroxypropionate; PHP), poly(3-hydroxyhexanoate; PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide; PLGA), polydioxanone, polyorthoester, polyether ester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazenes, PHA-PEG, chitosan, dextran, cellulose, heparin, alginate, inulin, starch, or glycogen is preferably used. However, the biocompatible or biodegradable material is not limited thereto.

In a preferred embodiment of the present invention, the membrane may be, but is not limited to, cellulose or collagen.

Finally, the method for preparing a xenograft animal model according to the present invention comprises a step [step (f)] of transplanting, into a subject animal, the lung cancer organoid immobilized with the membrane.

In an embodiment of the present invention, the subject animal may be, but is not limited to, a mouse, preferably an immunodeficient mouse.

In an embodiment of the present invention, the method for preparing a xenograft animal model according to the present invention may further comprise a step of removing the membrane that encapsulates the organoid, after the lung cancer organoid transplantation step.

In a case where the membrane is a cellulose membrane, the membrane that encapsulates the organoid may be removed 2 to 5 weeks after the organoid is transplanted into the subject animal. Preferably, membrane removal is preferably performed 3 weeks after transplantation. However, the present invention is not limited thereto. In a case where the period of time during which the organoid remains in the living body is shorter than the above range, there is a problem that there is no enough time for the organoid to settle to the epidermis of the subject animal; and in a case where the period of time during which the organoid remains in the living body is longer than the above range, there is a problem that inflammatory reaction occurs.

In still yet another aspect of the present invention, there is provided a patient-derived lung cancer organoid xenograft animal model prepared according to the method for preparing a xenograft animal model.

The xenograft animal model according to the present invention can be usefully used for studying lung cancer trends in specific patients from the viewpoints that histological properties which are characteristic of the patent's cancer tissue can be maintained, and problems, such as low transplantation rate into the living body, long time taken for transplantation, and relatively large amount of cancer tissue required for transplantation, which have been pointed out as problems of a conventional patient-derived cancer transplantation model, are remedied.

In still yet another aspect of the present invention, there is provided a method for analyzing therapeutic efficacy of an anticancer agent using a patient-derived lung cancer organoid xenograft animal model, comprising the steps of: (a) administering an anticancer agent to the patient-derived lung cancer organoid xenograft animal model; and (b) analyzing growth or metastasis of lung cancer cells in the animal model to determine therapeutic efficacy of the anticancer agent.

First, the analysis method according to the present invention comprises a step [step (a)] of administering an anticancer agent to the patient-derived lung cancer organoid xenograft animal model of the present invention. Specifically, in the method of administering an anticancer agent to a lung cancer-induced animal, in a case where a mouse is used, it is preferable to administer the anticancer agent to the tail vein of a lung cancer-induced mouse. However, the present invention is not limited thereto.

Next, the analysis method according to the present invention comprises a step [step (b)] of analyzing growth or metastasis of lung cancer cells in the animal model, to which the anticancer agent has been administered, to determine therapeutic efficacy of the anticancer agent. Specifically, the therapeutic efficacy of the anticancer agent may be analyzed by measuring expression levels of related genes or microvascular density depending on the type of lung cancer, and the growth or metastasis of the lung cancer cells may be visually observed or measured using a tool such as calipers. Thus, in a case where further growth or metastasis of the lung cancer cells is inhibited, it may be determined that the anticancer agent to be analyzed has efficacy as an anticancer agent.

In still yet another aspect of the present invention, there is provided a method for screening an anticancer agent using a patient-derived lung cancer organoid xenograft animal model, comprising the steps of: (a) administering an anticancer agent candidate to the patient-derived lung cancer organoid xenograft animal model; and (b) analyzing growth or metastasis of lung cancer cells in the animal model to determine therapeutic efficacy of the anticancer agent candidate.

As used herein, the term "anticancer agent candidate" refers to an unknown substance used in screening to examine whether it has inhibitory activity against growth or metastasis of tumor cells. The candidate includes, but is not limited to, chemicals, peptides, proteins, antibodies, and natural extracts. The candidate to be analyzed by the screening method of the present invention includes single compounds or mixtures of compounds (for example, natural extracts, or cell or tissue cultures). The candidate may be obtained from a library of synthetic or natural compounds. Methods of obtaining such a library of compounds are known in the art. A library of synthetic compounds is commercially available from Maybridge Chemical Co. (UK), Comgenex (USA), Brandon Associates (USA), Microsource (USA), and Sigma-Aldrich (USA), and a library of natural compound is commercially available from Pan Laboratories (USA) and MycoSearch (USA). The candidate may be obtained by a variety of combinatorial library methods known in the art, for example, biological libraries, spatially addressable parallel solid phase or solution phase libraries, synthetic library methods requiring deconvolution, one-bead one-compound library methods, and synthetic library methods using affinity chromatography selection. For methods for synthesizing a molecular library, those disclosed in DeWitt et al., Proc. Natl. Acad. Sci. U.S.A. 90, 6909, 1993; Erb et al. Proc. Natl. Acad. Sci. U.S.A. 91, 11422, 1994; Zuckermann et. al.., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994; and the like may be used. However, the present invention is not limited thereto.

First, the screening method according to the present invention comprises a step [step (a)] of administering an anticancer drug candidate to the patient-derived lung cancer organoid xenograft animal model. Specifically, in the method of administering an anticancer agent candidate to a lung cancer-induced animal, in a case where a mouse is used, it is preferable to administer the anticancer agent candidate to the tail vein of a lung cancer-induced mouse. However, the present invention is not limited thereto.

Next, the screening method according to the present invention comprises a step [step (b)] of analyzing growth or metastasis of lung cancer cells in the animal model, to which the anticancer agent candidate has been administered, to determine therapeutic efficacy of the anticancer agent candidate. Specifically, the therapeutic efficacy of the anticancer agent may be analyzed by measuring expression levels of related genes or microvascular density depending on the type of lung cancer, and the growth or metastasis of the lung cancer cells may be visually observed or measured using a tool such as calipers. Thus, in a case where further growth or metastasis of the lung cancer cells is inhibited, it may be determined that the anticancer agent candidate to be analyzed has efficacy as an anticancer agent.

In the method for culturing a 3-dimensional lung cancer organoid according to the present invention and the method for preparing a patient-derived xenograft animal model using the same, cancer cells obtained by cellization of cancer tissue collected from a lung cancer patient can be cultured so that a 3-dimensional organoid is formed, and organoids forming 3 dimensional structure can be transplanted while preserving its 3-dimensional shape for representing histological properties of their original patient tissues. In addition, the method for preparing a patient-derived xenograft animal model according to the present invention allows an animal model to be quickly prepared using a smaller number of organoid cells than conventional methods. In addition, the method for preparing an animal model of the present invention not only has a high success rate of lung cancer xenograft, but also can be usefully used for study of specific lung cancer patients and screening of the most appropriate anticancer agent.

EXAMPLES

Hereinafter, preferred examples are given to help to understand the present invention. However, the following examples are merely provided to more easily understand the present invention, and the scope of the present invention is not limited by the following examples.

Preparation Example

Experiments were conducted under approval from the Institutional Review Board (IRB) and the Animal Care Committee (ACC) of Asan Medical Center (Seoul, South Korea).

Human lung cancer samples were obtained from tissues excised during surgery for 7 lung cancer patients.

Examples

Example 1. 3-Dimensional Culture of Patient-Derived Lung Cancer Cells 1-1) Cellization of Patient-Derived Lung Cancer Tissue The samples in the Preparation Example were cellized according to a known protocol. Specifically, each of the samples in the Preparation Example was placed on a petri dish, and trimming was done using a surgical knife to provide only a cancer tissue portion. The cancer tissue was cut to 1 to 2 mm, transferred to a 15-ml conical tube, and pipetted vigorously 3 to 4 times with a washing solution (DMEM media+0.1% BSA). The resultant was left to stand for 1 minute so that the tissue precipitates due to gravity, and then the supernatant was removed. The above washing step was repeated 3 to 4 times until the tissue becomes clean.

Then, the same amount of digestion solution as the tissue was added thereto and reaction was allowed to proceed for 40 to 60 minutes in a 37° C. rotary incubator. After 20 minutes, a microscope (40 to 100 magnification) was used to identify whether single cells or cell clusters are clearly visible, and then the reaction time was determined. Washing was performed by addition of a washing solution, and then the supernatant was transferred to a new tube. The remaining tissue was subjected to further digestion. A step of performing centrifugation with 1200 rpm for 5 minutes at 4° C. and then removing the supernatant was repeated twice.

For the digestion solution, a collagenase solution prepared in a conventional manner was used, in which collagenase II (# Thermo 17101015) was used for intestinal cells, gastric cells, and lung cells, and collagenase D (# Roche 11088858001) was used for liver cells.

1-2) Culture of Lung Cancer Cells into Organoid

In Example 1-1), the pellet remaining after removal of the supernatant was resuspended, and then filtered through a 100-μm sieve. The filtered solution was centrifuged with 600 rpm for 3 minutes, and then the supernatant was removed. The pellet remaining after removal of the supernatant was resuspended in 50 μl of culture media, and then further resuspended by addition of 100 μl of MATRIGEL® (BD BIOSCIENCES®, San Jose, Calif, USA). Subsequently, 150 μl of the resuspended cell culture solution was dispensed into each well of a 6-well plate so that a dome shape is formed. Here, in a case where the tissue is present in a large amount, the amount of MATRIGEL® presented above is increased by 2 to 3 times to suspend the tissue, and then 150 μl of the solution was dispensed into each well in a dome shape.

The plate into which the dome-shaped cells had been dispensed was solidified in a 37° C. incubator for 10 to 15 minutes. Then, the plate was placed in 2 to 3 ml of the medium for lung cancer organoid so that the dome-shaped cells were sufficiently immersed, and culture was performed.

Composition of the medium for lung cancer organoid of the present invention is as shown in Table 1 below.

TABLE 1

| Composition | Stock Conc. | Final Conc. |
|---|---|---|
| DMEM/F-12 | | |
| B27 | 50× | 1× |
| N2 | 50× | 1× |
| hEGF | 100 mM | 50 ng/mL |
| hFGF | | 520 ng/mL |
| Y-27632 | | 10 μM |
| P/S | 100× | 1× |

Figure 2:
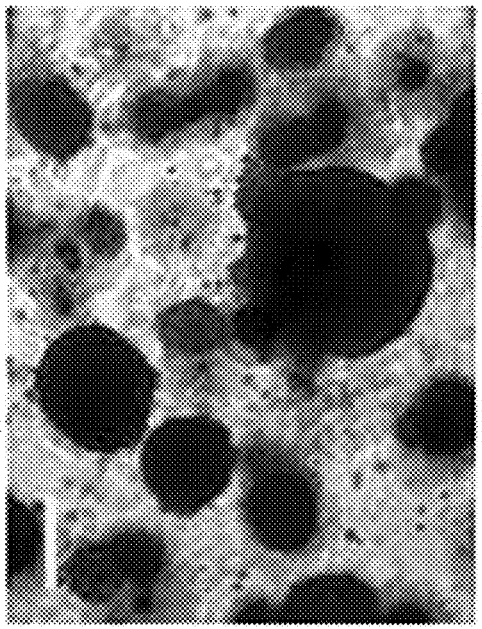
FIG. 2 illustrates photographs showing organoids cultured according to an embodiment of the present invention.
Figure 2:
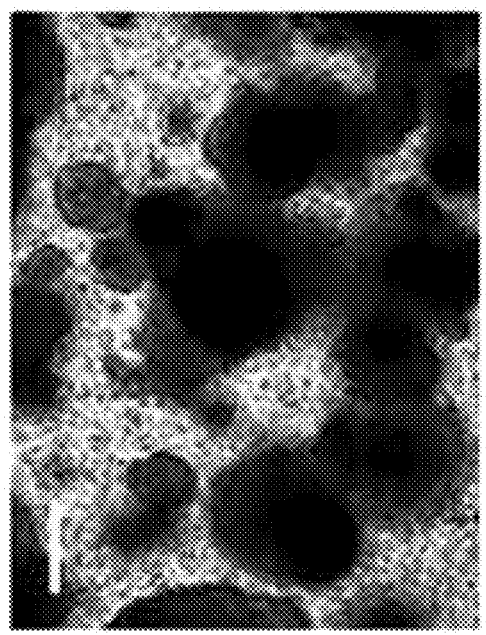
Figure 2:
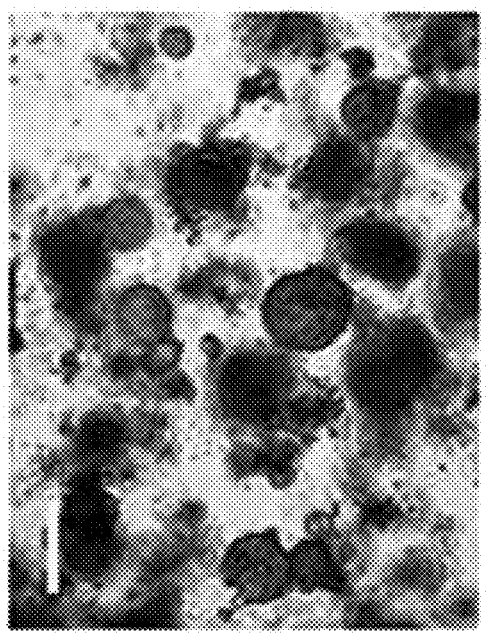

FIG. 2 illustrates results obtained by observing, under a microscope, lung cancer organoids cultured according to the Example of the present invention. From the results illustrated in FIG. 2, it can be seen that the cultured lung cancer organoids exhibit histomorphological properties which can be classified into adenosquamous cell carcinoma, squamous cell carcinoma, and small cell lung cancer (SCLC), respectively, and these organoids have preferably grown.

Example 2. Separation of Organoid and Enzymatic Dissociation 2-1) Separation of Organoid The medium for lung cancer organoid used for the culture in Example 1-2) was placed in a water bath and warmed up. Then, the medium in each well of the 6-well plate was removed. Subsequently, 500 μl of cold PBS was placed in each well, and the organoid-containing MATRIGEL® was removed from the plate. Subsequently, the MATRIGEL®/PBS mixture was transferred to a 15-ml conical tube, and the organoid was separated.

2-2) Enzymatic Dissociation

The organoid separated in Example 2-1) was centrifuged with 250×g for 3 minutes at 4° C., and then the supernatant was removed. The resultant was resuspended with PBS, and then centrifugation was performed again with 250×g for 10 minutes at 4° C. to separate the organoid from the MATRIGEL® layer. The supernatant and the MATRIGEL® were removed. Then, 1,000 to 2,000 μl of Trypsin/EDTA was placed in 3 wells of a 6-well plate, and reaction was allowed to proceed for 10 to 15 minutes in a rotary incubator. To the remaining 3 wells was added TrypLE™ Express, and reaction was allowed to proceed for 15 to 20 minutes in a rotary incubator. Here, the enzyme reaction time can be regulated while observing, with tapping, whether or not the organoid is well dissociated.

Next, 7 ml of the medium supplemented with 10% FBS was added thereto, and mixed well. Then, centrifugation was performed with 600 rpm for 3 minutes at 4° C., and the supernatant was removed. Depending on the pellet size, the pellet was mixed with the medium for lung cancer organoid and an appropriate amount of MATRIGEL®, and then the mixture was dispensed, in a dome shape, into each well of a 24-well plate. Here, based on 3 wells of the 24-well plate, the pellet was resuspended with 50 μl of the medium for lung cancer organoid, and then further resuspended by addition of 100 μl of MATRIGEL®. The resuspension was dispensed, in a dome shape, into each well, at an amount of 50 μl per well. Subsequently, the dispensed resuspension was solidified for 5 to 15 minutes in a 37° C. incubator. Then, the resultant at 500 1 each was placed in the medium for lung cancer organoid and incubation was performed.

Example 3. Preparation of Xenograft Mouse Model Using Patient-Derived 3-Dimensional Lung Cancer Organoid Cells 3-1) Histomorphological Analysis of Organoid The medium in three to four wells of the 24-well plate in Example 2-2) was removed, and 500 μl of cold PBS was placed in each well. The organoid-containing MATRIGEL® was removed from the plate. Subsequently, the MATRIGEL®/PBS mixture was transferred to a 15-ml conical tube, centrifugation was performed with 250×g for 3 minutes at 4° C., and then the supernatant was removed. PBS was added to the tube from which the supernatant had been removed and resuspension was performed. Then, centrifugation was performed with 250×g for 10 minutes at 4° C., to separate the organoid from the MATRIGEL® layer. The separated MATRIGEL® layer and the supernatant were completely removed.

Figure 3:
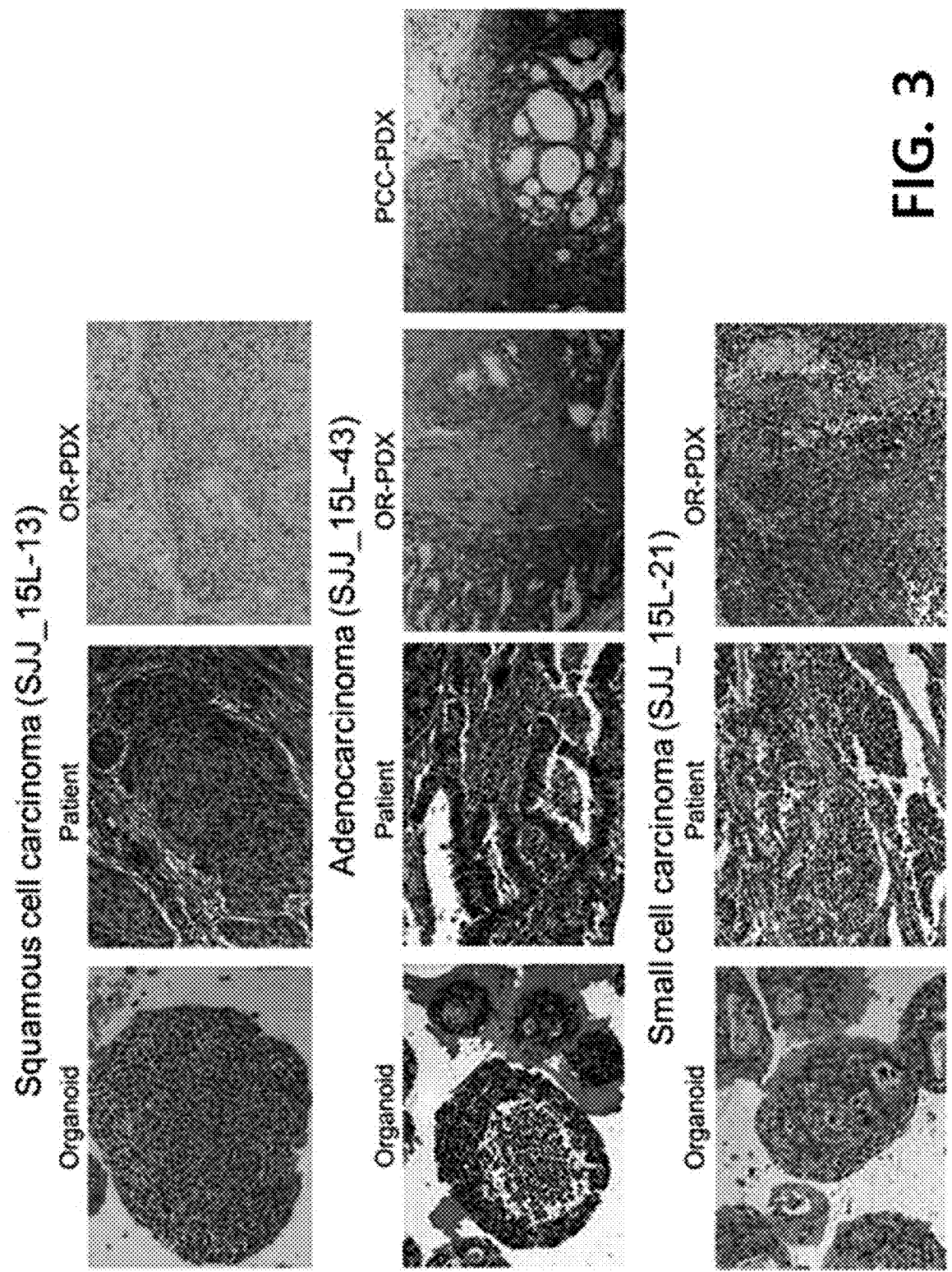
FIG. 3 illustrates photographs showing results of histomorphological analysis for xenograft animal models according to an embodiment of the present invention.
Figure 4:
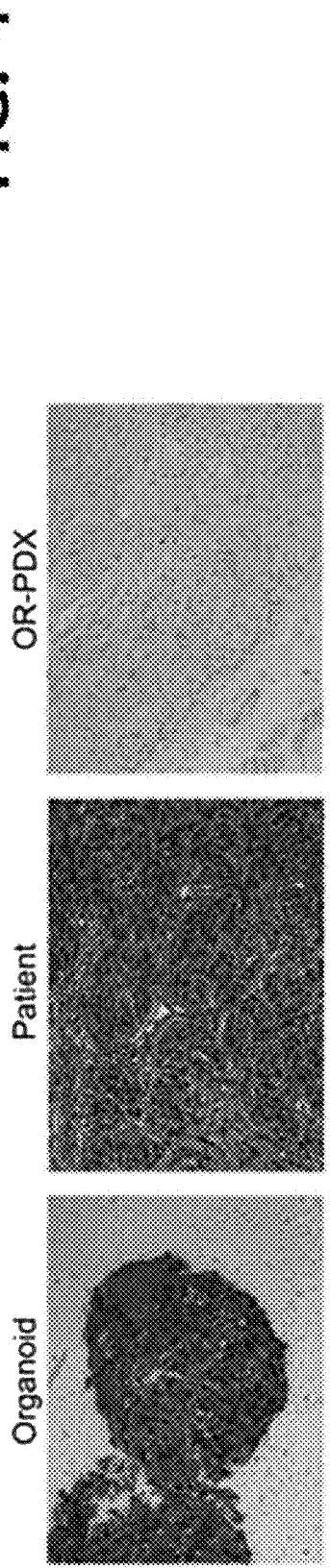
FIG. 4 illustrates photographs showing results of histomorphological analysis for xenograft animal models according to an embodiment of the present invention.
Figure 4:
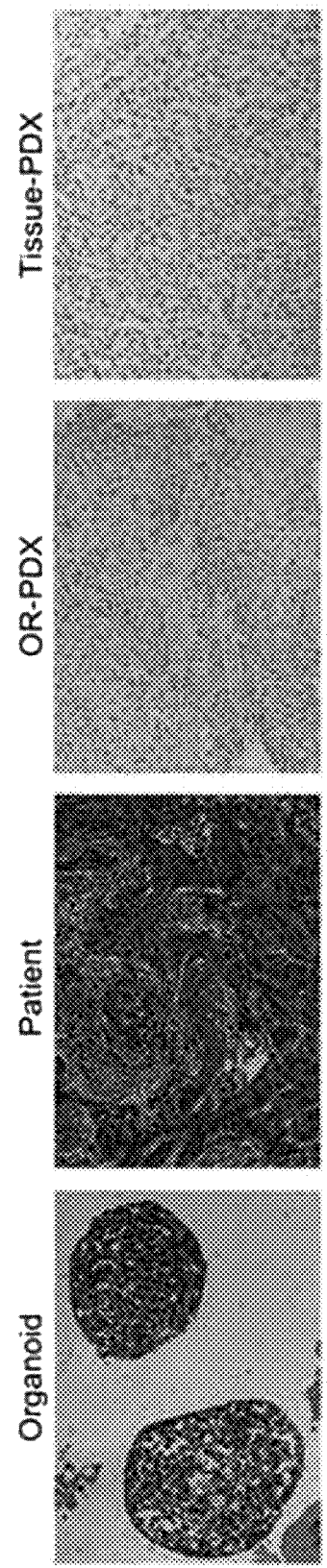

To the organoid, which the MATRIGEL® and the supernatant had been completely removed by the above centrifugation, was added an ethanol-containing fixing solution. Fixing was performed at 4° C. for 1 to 2 days. The fixed organoid was washed with PBS and then fixed again at room temperature for 1 hour by addition of 100% ethanol. Then, washing with PBS was performed, and the resultant was solidified by addition of 2% agarose gel and an extremely small amount of dye. The solidified agarose/organoid sample was wrapped in lens paper and then placed in a tissue cassette, from which a paraffin-embedded (PE) block was made using 56° C. paraffin. The block was cut to 4 m, stained with hematoxylin and eosin (H&M), and observed under a microscope. The results are illustrated in FIGS. 3 and 4. Histomorphological and pathological diagnosis was performed according to the WHO lung cancer classification criteria, and lung cancer of each sample was classified into squamous cell carcinoma, adenosquamous cell carcinoma, large cell carcinoma, or small cell lung cancer (SCLC). Based on the analysis results, cases where the organoid tissue histomorphologically matches the patient's tissue were selected and used for transplantation into mice.

3-2) Organoid Preparation

In the same manner as in Example 3-1), the MATRIGEL® was completely removed from the cultured lung cancer organoid in Example 2-2), and then the organoid for xenograft was prepared.

Specifically, the medium in three to four wells of a 24-well plate was removed, 500 μl of cold PBS was placed in each well, and the organoid-containing MATRIGEL® was removed from the plate. Then, the MATRIGEL®/PBS mixture was transferred to a 15-ml conical tube and centrifugation was performed with 250×g for 3 minutes at 4° C. Then, the supernatant was removed. PBS was added to the tube from which the supernatant had been removed and resuspension was performed. Then, centrifugation was performed with 250×g for 10 minutes at 4° C., to separate the organoid from the MATRIGEL® layer. The separated MATRIGEL® layer and the supernatant were completely removed.

To the pellet were added 10 μl of the medium and 40 μl of MATRIGEL®. The organoid-containing MATRIGEL® solution was placed on the membrane with a blue tip. Here, as the membrane, a water-soluble cellulose membrane or a biodegradable membrane was used, with the membrane having a square shape of about 3 to 5 mm being preferred. The organoid-placed membrane was solidified for 10 minutes in a 37° C. incubator.

3-3) Transplantation into Mice 6- to 8-week-old NOD-SCID mice (Charles River Laboratories, Wilmington, MA, USA) were anesthetized with a mixture of anesthetics, 40 mg/kg of Zoletil (Virvac laboratories BP 27-06511 Carros, France) and 5 mg/kg of Rompun (Bayer, South Korea). Excision was performed so that only the epidermis area is exposed. Subsequently, the excised portion was carefully lifted and the membrane bottom portion of the organoid prepared in Example 3-2) was positioned therein to face the mouse dermis. The organoid was placed deep therein and then suture was performed. The membrane was checked for its visible location for 3 weeks. After 3 weeks, the transplanted cellulose membrane was removed, and the organoid was maintained for 12 to 14 weeks until lung cancer grew in mice. After 7 to 11 weeks, the cancer was visually identified.

Cancer tissues produced for 12 to 14 weeks were subjected to histomorphological analysis in the same manner as 3-2), and the results are illustrated in FIGS. 3 and 4. When the histomorphological results between the patient and the xenograft (OR-PDX) showed the same morphology, the transplantation was counted as successful.

Comparative Example

Comparative Example 1. Primary Culture of Lung Cancer Cells from Patient-Derived Lung Cancer Tissue and Preparation of Xenograft Animal Model Each of the samples in the Preparation Example was excised with scissors and incubated for 1 hour with addition of DMEM/F12 medium containing 1 mg/mL of type IV collagenase (Sigma Chemical Co., St. Louis, MO, USA). Subsequently, the tissue was washed with a washing solution containing 0.1% BSA in DMEM/F12, and then primary culture of the lung cancer cells was performed in a plastic dish coated with collagen using the medium for lung cancer organoid. Thereafter, medium replacement was performed and culture was performed for 5 to 14 days. Then, the passage cells were obtained to give primary cultured lung cancer cells.

The primary cultured lung cancer cell line was transplanted into 6- to 8-week-old NOD-SCID mice (Charles River Laboratories, Wilmington, MA, USA).

More specifically, $1 \times 10^6$ patient-derived primary cultured tumor cells were resuspended in 100 μl of MATRIGEL® (BD BIOSCIENCES®, San Jose, Calif., USA) and injected into the subcutaneous layer of the back of the NOD/SCID mice. After 3 to 4 months which is at the time when the tumor size exceeds 1 cm$^3$, the mice were anesthetized by an intraperitoneal injection of a ZOLETIL™ (VIRBAC™, Virvac laboratories BP 27-06511 Carros, France; 40 mg/kg) and ROMPUN™ (BAYER™, South Korea; 5 mg/kg) mixture. Then, the tumor was surgically cut and checked for successful transplantation.

Transplantation was performed in different parts of the same mouse using the organoid transplantation method (OR-PDX) of the Example and the primary cultured cell transplantation method (PCC-PDX) of Comparative Example 1. Then, growth of the tumor tissue was visually identifiable. As illustrated in FIG. 5, all samples were successful in a case where the OR-PDX method is used (left); and only SJJ-15L-29 and SJJ-15L-43 samples were successful in a case where the PCC-PDX method is used.

Comparative Example 2. Preparation of Xenograft Animal Model Using Patient-Derived Lung Cancer Tissue Tissue extracted from a patient at the time of surgery was obtained, and trimming was done using a surgical knife in a petri dish to provide only a cancer tissue portion. The cancer tissue was cut to 1 to 2 mm and then transferred to a 15-ml conical tube. Pipetting was performed vigorously 3 to 4 times with a washing solution containing 0.1% BSA in DMEM/F12. The resultant was left to stand for 1 minute so that the tissue precipitates due to gravity, and then the supernatant was removed. The above washing step was repeated 3 to 4 times until the tissue becomes clean. Among the cut cancer pieces, 3 to 4 pieces were used for transplantation.

The prepared cancer tissue was transplanted into 6- to 8-week-old NOD/SCID mice (Charles River Laboratories, Wilmington, MA, USA).

More specifically, the epidermis of the NOD/SCID mice was excised and 3 to 4 pieces of cancer tissue were placed therein at the same time. Then, suture was performed. After 3 to 4 months, anesthesia was performed by injecting a mixture of Zoletil and Rompun as described above. Then, the tumor was surgically cut and checked for successful transplantation.

[Experimental Example] Identification of Success of Xenograft Model Through Histomorphological Analysis In order to identify effects of transplantation performed according to the organoid transplantation method of the present invention (Example, OR-PDX), morphological comparative analysis was performed on tissues from the model of the present invention and the xenograft mouse models prepared by the conventional primary cultured cell injection method (Comparative Example 1, PCC-PDX) and the direct transplantation method of patient-derived lung cancer tissue (Comparative Example 2, Tissue-PDX), respectively.

Specifically, 7 lung cancer cell samples were transplanted into immunodeficient mice using the methods of the Example and the Comparative Examples, and then 3 to 4 months were allowed to pass until the transplanted cells grow. Then, the transplanted tumor tissue was surgically cut and fixed in cold 2% formaldehyde for 4 hours. The cut tumor tissue was embedded in 56° C. paraffin. The PE block was cut into 4 m and stained with H&E. Pathological diagnosis was performed according to the WHO lung cancer classification. When the histomorphological results between the patient and the xenograft animal (OR-PDX, PCC-PDX, or Tissue-PDX) showed the same morphology, the transplantation was counted as successful.

The results obtained by transplanting the 7 tissue samples into the mice using different methods are shown in Table 2 below, and some of the histomorphological observation results for the respective samples are illustrated in FIGS. 3 and 4.

TABLE 2

| Sample | OR-PDX (Example) | PCC-PDX (Comparative Example 1) | Tissue-PDX (Comparative Example 2) |
|---|---|---|---|
| SJJ-15L13 | O | X | X |
| SJJ-15L21 | O | X | X |

TABLE 2-continued

| Sample | OR-PDX (Example) | PCC-PDX (Comparative Example 1) | Tissue-PDX (Comparative Example 2) |
|---|---|---|---|
| SJJ-15L28 | O | X | X |
| SJJ-15L29 | O | O | O |
| SJJ-15L42 | O | X | O |
| SJJ-15L43 | O | O | X |
| SJJ-15L51 | O | X | X |

(OR-PDX: xenograft animal obtained by 3-dimensional transplantation of a lung cancer organoid according to an embodiment of the present invention, PCC-PDX: xenograft animal obtained by using primary cultured lung cancer cells according to Comparative Example 1 of the present invention, Tissue-PDX: xenograft animal obtained by direct transplantation of patient lung cancer tissue according to Comparative Example 2 of the present invention)

As shown in Table 2 above, all 7 samples were successfully transplanted in a case where the organoid transplantation method (OR-PDX) of the present invention is used; however, only two samples were successfully transplanted for each of PCC-PDX and Tissue-PDX. It was found that in a case of SJJ-15L29 sample which is relatively easy to transplant, successful tissue transplantation is achieved in all 3 methods; however, in a case of 4 samples which are difficult to transplant, successful tissue transplantation is achieved only in the OR-PDX method.

Therefore, it can be seen that the method for preparing a xenograft model according to the present invention exhibits a remarkably increased transplantation success rate as compared with the conventional tissue transplantation methods.

The foregoing description of the present invention is provided for illustration. It will be understood by those skilled in the art that various changes and modifications can be easily made without departing from the technical spirit or essential features of the present invention. Therefore, it is to be understood that the above-described examples are illustrative in all aspects and not restrictive.

The invention claimed is:

1. A method for preparing a patient-derived lung cancer organoid xenograft animal model, comprising the steps of:
 (a) culturing lung cancer cells, which have been obtained by cellizing lung cancer tissue isolated from a lung cancer patient, with a cell culture substrate, to obtain a lung cancer organoid;
 (b) subjecting the obtained organoid to treatment with an enzyme and then allowing reaction to proceed;
 (c) adding, to the lung cancer organoid after step (b), a cell culture substrate, and performing culture so that a 3-dimensional lung cancer organoid is formed;
 (d) removing the cell culture substrate from the 3-dimensional lung cancer organoid;
 (e) encapsulating the 3-dimensional lung cancer organoid, from which the cell culture substrate has been removed, in a membrane and then solidifying the same; and
 (f) transplanting, into a subject animal, the 3-dimensional lung cancer organoid obtained in step (e), wherein the transplanting into a subject animal does not comprise injection of the 3-dimensional lung cancer organoid by syringe.

2. The method according to claim 1, wherein the cell culture substrate includes at least one selected from the group consisting of hydrogel based on extracellular matrix extracted from the Engelbreth-Holm-Swarm mouse sarcoma collagen, alginate, agarose, gelatin, fibrin, hyaluronic acid, and chitosan.

3. The method according to claim 1, wherein the membrane is at least one biocompatible or biodegradable membrane selected from the group consisting of hyaluronic acid, polyester, polyhydroxyalkanoates (PHAs), poly($\alpha$-hydroxyacid), poly($\beta$-hydroxyacid), poly(3-hydroxybutyrate-co-valerate) (PHBV), poly(3-hydroxypropionate) (PHP), poly(3-hydroxyhexanoate) (PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide) (PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazenes, copolymers of polyhydroxyalkanoates and polyethylene glycols (PHA-PEG), ethylene vinyl alcohol copolymer (EVOH), polyurethane, silicone, polyester, polyolefin, polyisobutylene and ethylene-alphaolefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, acrylonitrile butadiene styrene (ABS) resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, alginate, inulin, starch, and glycogen.

4. The method according to claim 1, wherein the subject animal is an immunodeficient mouse.

5. The method according to claim 1, further comprising:
 a step of removing the 3-dimensional lung cancer organoid-encapsulating membrane, after transplantation of the 3-dimensional lung cancer organoid.

6. The method according to claim 1, wherein the transplanting, into a subject animal, comprises placing the 3-dimensional lung cancer organoid into an opening formed by excising a portion of tissue from the subject animal.

* * * * *